(12) United States Patent
Remy

(10) Patent No.: US 6,468,550 B1
(45) Date of Patent: Oct. 22, 2002

(54) USE OF AN IONIC CONDUCTOR IN ORDER TO IMPROVE PHOTOCHROMISM, AND COMPOSITION COMPRISING IT

(75) Inventor: Christophe Remy, Thomery (FR)

(73) Assignee: L'Oreal, S.A., Paris (FR)

( * ) Notice: Subject to any disclaimer, the term of this patent is extended or adjusted under 35 U.S.C. 154(b) by 265 days.

(21) Appl. No.: 09/139,280

(22) Filed: Aug. 25, 1998

(30) Foreign Application Priority Data

Aug. 26, 1997 (FR) ............................................ 97 10658

(51) Int. Cl.$^7$ ............................ A61K 7/00; A61K 7/04; A61K 7/21; A61K 7/25; A61K 7/35

(52) U.S. Cl. ........................... 424/401; 424/61; 424/63; 424/64; 424/69; 424/70.6; 424/70.7; 424/617; 424/677; 424/679; 424/680; 424/696; 424/697

(58) Field of Search ......................... 424/63, 401, 677, 424/679, 680, 696, 697, 617, 59, 64, 69, 70.1, 70.7

(56) References Cited

U.S. PATENT DOCUMENTS

| | | | | |
|---|---|---|---|---|
| 4,724,138 A | * | 2/1988 | Duffy et al. | |
| 4,994,088 A | * | 2/1991 | Ando et al. | |
| 5,176,905 A | * | 1/1993 | Ohno et al. | |
| 5,543,136 A | * | 8/1996 | Aldous | |
| 5,750,124 A | * | 5/1998 | Gohla et al. | |
| 5,928,655 A | * | 7/1999 | Avalle | |

FOREIGN PATENT DOCUMENTS

| | | | |
|---|---|---|---|
| DE | 4 302 896 | * | 8/1994 |
| EP | 0 359 909 | * | 3/1990 |
| EP | 0 526 712 | * | 2/1993 |
| EP | 0 624 553 | * | 11/1994 |
| FR | 1 604 929 | * | 6/1972 |
| FR | 2 209 717 | * | 7/1974 |
| JP | 5-17152 | * | 1/1993 |

OTHER PUBLICATIONS

Derwent Publications, Ltd., Japanese Patent Application No. 09030933, Section Ch, Week 9715, 1997.*
R.W. Fitzpatrick et al., "Amorphous and Crystalline Titanium and Iron–Titanium Oxides in Synthetic Preparations, at Near Ambient Conditions, and in Soil Clays", Clay and Clay Minerals, vol. 26, No. 3, pp. 189–201, 1978.*
English Language Derwent Abstract of DE 4 302 896.*
English Language Derwent Abstract of FR 1 604 929.*
English Language Derwent Abstract of FR 2 209 717.*
English Language Derwent Abstract of JP 5017152.*

* cited by examiner

Primary Examiner—Russell Travers
Assistant Examiner—Alysia Berman
(74) Attorney, Agent, or Firm—Finnegan, Henderson, Farabow, Garrett & Dunner, L.L.P.

(57) ABSTRACT

A method of improving the photochromishm of a composition comprising at least one photochromic compound with an ionic conductor, and the composition thereof. The composition may, in particular, be in the form of a care and/or make-up product for the skin, a suncare or self-tanning product, or a haircare product.

53 Claims, No Drawings

USE OF AN IONIC CONDUCTOR IN ORDER TO IMPROVE PHOTOCHROMISM, AND COMPOSITION COMPRISING IT

Applicant references herein the patent application of CHRISTOPHE REMY for PROCESS FOR THE PREPARATION OF PHOTOCHROMIC TITANIUM OXIDE, COMPOUND OBTAINED AND COMPOSITION COMPRISING IT filed on even date herewith and incorporates the disclosure thereof specifically by reference herein.

The present invention relates to the improvement of the photochromic properties of an initially photochromic inorganic compound, and to its application in the field of cosmetic compositions in particular.

Cosmetic compositions, in particular make-up compositions such as free or compact powders, foundations, blushers or eye-shadows, lip compositions or nail varnishes, consist of a suitable vehicle and various colorants intended to impart some degree of colour to the said compositions before and/or after they are applied to the skin, the mucous membranes, the mucocutaneous tissues and/or parts of the exoskeleton, for example the nails or the hair.

A fairly limited range of colorants is presently used to create colours, in particular lakes, inorganic pigments or pearlescent pigments. Lakes allow vivid colours to be obtained, but are for the most part unstable with respect to light, temperature or pH. Some of them also have the drawback of staining the skin unattractively after they have been applied, as a result of the colorant being leached. Conversely, inorganic pigments, in particular inorganic oxides, are highly stable but give somewhat dull and pale colours. In order to obtain coloured effects, use may also be made of pearlescent pigments whose. colours are varied, albeit never intense, which make it possible to obtain iridescent but, most often fairly weak effects.

It has therefore been proposed to use photochromic compounds in make-up or haircare compositions, so as to obtain attractive and varied changes in the colour effect of make-up for the skin and/or the hair.

Photochromic compounds are compounds which have the property of changing colour when they are exposed to a light source, then of returning to their initial colour, or a similar colour, when they are no longer being exposed. In particular, compounds of this type have a particularly advantageous application in cosmetic compositions, in particular in make-up compositions such as foundations and blushers or eye-shadows. Indeed, it has been found that the make-up effect of skin which has been made up differs depending on. whether the illumination is natural or artificial. Thus, make-up applied under artificial illumination will appear lighter under natural light. Conversely, make-up applied out of doors will appear darker in a place where the illumination is artificial.

In particular, it has been proposed to use organic photochromic compounds, for example-compounds of the spiropyran or naphthoxazine families.

These photochromic compounds are particularly advantageous since they enable the support to which they are applied to change colour rapidly when the support is exposed to UV, for example, with a rapid return to the initial colour when it is no longer being exposed to UV.

Mention may thus be made of French patent FR1604929, which describes cosmetic compositions, in particular for the hair and in aerosol form, which contain phototropic compounds such as nitrobenzylpyridines, thiosemicarbazones or spiropyran derivatives. After these compositions have been sprayed onto the hair and exposed to sunlight, a blue violet coloration is obtained which returns to pale yellow in darkness.

Cosmetic compositions comprising particular inorganic photochromic compounds, selected from metal oxides, their hydrated forms and their complexes, have also been proposed, for example by European patent EP359909. In particular, this document mentions the use of titanium oxide, treated so as to make it photochromic, in make-up compositions such as powders and foundations.

However, it has been observed that, even though they make it possible to obtain a make-up which seems to keep a constant colour irrespective of the nature of the; illumination, these photochromic compounds, in particular inorganic ones, nevertheless do not make it possible to obtain a true change in the colour of the make-up, or in other words. a true change in the make-up effect.

Furthermore, it has also been observed that, when it is no longer being exposed to light, the colour of the make-up does not always return acceptably to its initial colour, and in particular does not return completely to a colour identical to the initial colour.

The object of the invention is to provide a particular process for improving the photochromism, that is to say the photochromic properties, of an initially photochromic inorganic compound.

The photochromic properties of a compound can be characterized using trichromatic coordinates (L, a and b) in the way described before the examples. These coordinates make it possible, in particular, to determine the parameters $\Delta E30$ and $\Delta(\Delta E)$ which will be used in the present application to characterize the photochromism of the compounds, according to the invention and outside the scope of the invention.

In general, the higher the parameter $\Delta E30$, the more capable the compound is to change colour after being exposed. The higher the parameter $\Delta(\Delta E)$ is, the greater is the ability of the compound to return to its initial colour.

Thus, the object of the invention is therefore, in particular, to improve the parameters $\Delta E30$ and $\Delta(\Delta E)$ of the composition, that is to say to obtain the highest possible parameters.

The present invention therefore relates to the use of an ionic conductor in a composition comprising an inorganic photochromic compound, in order to improve the photochromism of the composition.

The invention also relates to a composition comprising at least one inorganic photochromic compound and at least one ionic conductor.

One advantage of the invention is that it makes it possible, in the cosmetic compositions according to the invention, to use an amount of photochromic compositions which is smaller than that used in the prior art, while obtaining a comparable make-up effect and covering power.

Another advantage of the invention is that it makes it possible, for the same amount of photochromic compounds, to obtain improved photochromic properties, that is to say an enhanced colour change and/or a return to the initial colour which is also enhanced.

Without being limited by the present explanation, the mechanism making it possible to improve the photochromic properties of a given compound may be as follows. An iron doped photochromic titanium oxide will be considered. When exposed to UV, it can be considered that the cation $Fe^{3+}$ will give up an electron to an entity X which will be converted into an entity $X^-$, responsible for the colour change of the said photochromic compound. It may be assumed that, during a second phase, electrons in the valence band of the titanium oxide will then be moved to the conduction band, consequently generating both free electrons, which can be picked up by X to form X⁻, and electron vacancies in the, valence band, which are also referred to as positive "holes", that is to say a vacant state in an energy band corresponding to a region with a negative charge in deficit.

The invention involves promoting the transfer of electrons within photochromic titanium oxide so as to improve its photochromic properties.

The term "ionic conductor" is used according to the invention to mean any compound which can be separated into cations and anions when it is dissolved in water or an aqueous medium.

The ionic conductor is preferably selected from the salts of alkali or alkaline-earth metals; mention may in particular be made of the chlorides of sodium, lithium, potassium, and the sulphates of magnesium or calcium, alone or as a mixture.

The ionic conductor may be incorporated into the composition in an amount which can be readily determined by the person skilled in the art on the basis of his general knowledge, in order to obtain the desired effect; this amount may preferably range from 0.5 to 30% by weight relative to -the total weight of the composition, and more preferably in an amount of from 1 to 20% by weight.

According to a preferred embodiment of the invention, the ionic conductor is incorporated, such as by simple addition, into a cosmetic composition containing a photochromic compound and a cosmetically acceptable medium, to improve the photochromism of the photochromic compound. To improve the photochromism in accordance with the present invention, there is no need to heat treat at a temperature between about 200 and 400° C. the cosmetic composition after incorporation, such as by, simple addition, of the ionic conductor.

The composition furthermore comprises at least one photochromic inorganic compound, which may be selected from any of the prior art photochromic compounds that can be used in the relevant field of application.

Mention may in particular be made of metal oxides or hydrates, as well as doped aluminosilicates.

Among the metal oxides, the hydrated forms of the said oxides and their complexes, mention may be made of those described in European patent EP359909, the disclosure of which is hereby incorporated specifically by reference, and in particular the oxides of titanium, niobium, silicon, aluminium, zinc, hafnium, thorium, tin, thallium, zirconium, beryllium, cobalt, calcium and magnesium.

The oxides and hydrated oxides of titanium, aluminium, zinc, zirconium, calcium and magnesium are more preferred.

More preferably, use will be made of titanium dioxide which can be rendered photochromic using a metal selected from iron, chromium, copper, nickel, manganese, cobalt, molybdenum, as such or in the form of a salt such as sulphate, a chlorate, a nitrate or an acetate.

Among doped aluminosilicates, mention may be made of those described in the French patent application 96FR-15451 which has not yet been published. These aluminosilicates preferably have a structure of the type: $R_8Al_6Su_6O_{24}X_n$ in which:

R represents an element selected from Na, K, Cs, Rb, Li, Ag or Ca; R preferably represents Na; and X represents at least one dopant elements as defined above, n ranges from 1 to 5, more preferably from 1 to 3.

Among these compounds, mention may in particular be made of those, of the sodalite family, whose formula is: $Na_8Al_6Si_6O_{24}X_2$, in which $X_2$ represents at least one halogen anion, and in particular $Cl_2$, $ClBr$, $I_2$ or $Br_2$.

The photochromic compound may be incorporated into the composition in an amount which can be readily determined by the person skilled in the art on the basis of his general knowledge, and which may preferably range from 0.01 to 30% by weight relative to the total weight of the composition, more preferably in an amount of from 1 to 15% by weight.

The composition according to the invention may preferably be in the form of a cosmetic composition, in particular in the form of a product to be applied to the mucous membranes, the mucocutaneous tissues and/or the keratinous tissues, such as the skin and parts of the exoskeleton (nails, eyelashes, eyebrows, body hair and head hair).

In particular, this composition may be a care and/or make-up product for the skin, a suncare or self-tanning product, or even a haircare product.

The compounds according to the invention find a particular application in the field of lip compositions, foundations, blushers or eyeshadows, eyeliners, mascaras and nail varnishes, in particular aqueous, aqueous-alcoholic or solvent-based ones.

The composition according to the invention therefore comprises a cosmetically acceptable medium, that is to say a medium which is compatible with all the keratinous materials such as the skin, the nails, the hair, the eyelashes and eyebrows, the mucous membranes and the mucocutaneous tissues, and any other cutaneous region of the body and the face.

The medium may comprise or be in the form of, in particular, a suspension, a dispersion or a solution in an aqueous or aqueous-alcoholic medium, optionally thickened or gelled; an oil-in-water, water-in-oil or multiple emulsion; a gel or a foam; an emulsified A gel; a dispersion of vesicles, in particular lipid vesicles; a two-phase or multi-phase lotion; or a spray.

The person skilled in the art will be able to choose the suitable pharmaceutical form, as well as the method of preparing it, on the basis of his general knowledge, while taking into account both the nature of the constituents which are used, in particular their solubility in the support, and the application envisaged for the composition.

Preferably, the composition according to the invention comprises an aqueous phase, and may therefore in particular be in the form of a dispersion, an emulsion, a lotion, a gel or an aqueous or aqueous-alcoholic solution.

However, the presence of an aqueous or hydrophilic phase is not necessary for implementing the invention; the invention may thus also be implemented in an anhydrous composition.

Thus, the composition according to the invention may comprise an aqueous phase which may comprise water, a floral water such as cornflower water, and/or a mineral water such as l'eau de Vittel, les eaux du bassin de Vichy, l'eau d'Uriage, l'eau de la Roche Posay, l'eau de la Bourboule, l'eau d'Enghien-les-Bains, l'eau de Saint Gervais-les-Bains, l'eau de Neris-les-Bains, l'eau d'Allevar-les-Bains, l'eau de Digne, l'eau de Lucas, l'eau de Maizieres, l'eau de Neyrac-les-Bains, l'eau de Lons-le-Saunier, les Eaux Bonnes, l'eau de Rochefort, l'eau de Saint Christau, l'eau des Fumades and l'eau de Tercis-les-bains.

The aqueous phase may comprise from 0% to 14% by weight, relative to the total weight of the aqueous phase, of a $C_2$–$C_6$ lower monoalcohol and/or of a polyol such as glycerol, butylene glycol, isoprene glycol, propylene glycol or polyethylene glycol.

When the composition according to the invention is in the form of an emulsion, it may optionally furthermore comprise a surfactant, preferably in an amount ranging from 0.01 to 30% by weight relative to the total weight of the composition.

Among the anionic surfactants which may be used, alone or as a mixture, mention may. in particular be made of alkali metal salts, armtmonium salts, amine salts or amino alcohol salts of the following compounds: alkyl sulphates, alkyl ether sulphates, alkylamide sulphates and ether sulphates, alkylarylpolyether sulphates, monoglyceride sulphates, alkylsulphonates, alkylamide sulphonates, alkylaryl sulphonates, α-olefin sulphonates, paraffin sulphonates, alkyl sulphosuccinates, alkyl ether sulphosuccinates, alkylamide sulphosuccinates, alkylsulphosuccinamates, alkyl sulphoacetates, alkyl polyglycerol. carboxylates, alkyl phosphates/alkyl ether phosphates, acyl sarcosinates, alkylpolypeptidates, alkylamidopolypeptidates, acyl isethionates, and alkyl laurates. The alkyl or acyl radical in all of these compounds generally denotes a chain of from 12 to 18 carbon atoms. Mention may also be made of soaps and fatty acid salts such as oleic acid, ricinoleic acid, palmitic acid, stearic acid, coconut oil acid or hydrogenated coconut oil acid and, in particular, amine salts such as amine stearates; acyl lactylates in which the acyl radical comprises 8–20 carbon atoms; carboxylic acids of polyglycol ethers corresponding to the formula: Alk-$(OCH_2-CH_2)_{n-2}OCH-COOH$ in acid or salified form, in which the substituent Alk corresponds to a straight chain having 12 to 18 carbon atoms and in which n is an integer ranging from 5 to 15.

Among the non-ionic surfactants which may be used, alone or as a mixture, mention may in particular be made of: polyethoxylated, polypropoxylated or polyglycerolated fatty acids, alkylphenols and alcohols which have a fatty chain containing 8 to 18 carbon atoms; copolymers of ethylene oxide and of propylene oxide, condensates of ethylene oxide and of propylene oxide with fatty alcohols, polyethoxylated fatty amides, polyethoxylated fatty amines, ethanolamides, fatty acid esters of glycol, fatty acid esters of oxyethylenated or. non-oxyethylenated sorbitan, fatty acid esters of saccharose, fatty acid esters of polyethylene glycol, phosphoric triesters, fatty acid esters of glucose derivatives; alkyl polyglycosides and alkylamides of amino sugars; condensation products of an a-diol, of a monoalcohol, of an alkylphenol, of an amide or of a diglycolamide with glycidol or a glycidol precursor.

The composition according to the invention may also comprise 0 to 5% by weight, relative to the total weight of the emulsion,. of at least one co-emulsifier which may be selected from oxyethylenated sorbitan monostearate, fatty alcohols such as stearyl alcohol or cetyl alcohol, or fatty acid esters of polyols such as glyceryl stearate.

The composition according to the invention may furthermore comprise one or more thickeners in preferred concentrations ranging from 0 to 6% by weight, relative to the total weight of the emulsion. The thickening agent may be selected from:

polysaccharide biopolymers such as xanthan gum, carob gum, guar gum, alginates, modified celluloses such as hydroxyethylcellulose, methylcellulose, hydroxypropylcellulose and carboxymethylcellulose, starch derivatives, cellulose ether derivatives containing quaternary ammonium groups, and cationic polysaccharides;

synthetic polymers, for instance polyacrylic acids such as polyglyceryl (meth)acrylate polymers such as HISPA-GEL or LUBRAGEL from the companies Hispano Quimica or u Gardian, polyvinylpyrrolidone, polyvinyl alcohol, crosslinked polymers of acrylamide and of ammonium acrylate such as PAS 5161 or BOZEPOL C from Hoechst; acrylate/octylacrylamide copolymers such as DERMACRYL from National Starch; polyacrylamide-based polymers such as SEPIGEL 305 from Seppic, crosslinked polymers of acrylamide and of methacryloyloxyethyltrimethylammonium chloride such as SALCARE SC 92 from Allied Colloids, magnesium aluminium silicate.

Depending on the application envisaged, the composition may furthermore comprise a film-forming polymer. This is, in particular, the case when it is desired to prepare a composition of the nail varnish, mascara or eye-liner type or a haircare composition of the lacquer type.

The polymers may be dissolved or dispersed in the cosmetically acceptable medium. In particular, the polymer may be present in the form of a solution in an organic solvent or in the form of an aqueous dispersion of film-forming polymer particles.

The polymer may be selected from nitrocellulose, cellulose acetobutyrate, polyvinyl butyrals, alkyl resins, polyesters, acrylics, vinyls and/or polyurethanes.

Mention may, in particular, be made of the copolymers of (meth)acrylic acid and of at least one ester monomer of linear, branched or cyclic (meth)acrylic acid and/or of at least one amide monomer of linear, branched or cyclic, mono- or disubstituted (meth)acrylic acid; (meth)acrylic acid/tert-butyl(meth)acrylate and/or isobutyl (meth)acrylate/ $C_1$-$C_4$ alkyl(meth)acrylate copolymers; (meth)acrylic acid/ethyl acrylate/methyl methacrylate terpolymers and tetrapolymers; methyl methacrylate/butyl or ethyl acrylate/hydroxyethyl or 2-hydroxypropyl acrylate or methacrylate/(meth)acrylic acid tetrapolymers; copolymers of acrylic acid and of $C_1$-$C_4$ alkyl methacrylate; terpolymers of vinylpyrrolidone, of acrylic acid and of $C_{1-20}$ alkyl methacrylate; amphoteric copolymers; vinyl esters of branched acids; vinyl esters of benzoic acid; copolymers of (meth) acrylic acid and of at least. one olefinic monomer; copolymers of vinyl monoacid and/or of allylic monoacid.

Among the resins, mention may be made of resins of the arylsulphonamide formaldehyde or arylsulphonamide epoxy type; resins of the acrylic, styrene, styreneacrylate and vinylacrylate type.

The composition may also comprise at least one plasticizer, such as tricresyl phosphate, benzyl benzoate, triethyl citrate, tributyl citrate, triethyl acetyl citrate, 2-triethylhexyl acetyl citrate, camphor; glycol ethers; castor oil oxyethylenated with 40 mol of ethylene oxide; propylene glycol; butyl glycol; ethylene glycol monomethyl ether acetate; propylene glycol ethers; ester ethers of propylene glycol and ethylene glycol; esters of diacids such as diethyl, dibutyl and diisopropyl phthalates and adipates, diethyl and dibutyl tartrates, diethyl and dibutyl succinates, diethyl and dibutyl sebacates, diethyl, dibutyl and 2diethylhexyl phosphates, diethyl or dibutyl acetyl citrate; glycerol esters. The plasticizers may generally be present at a level ranging from 1% to 40% by weight relative to the total weight of the composition.

The composition according to the invention may also comprise a fatty phase, in particular comprising fatty substances which are liquid at 25° C., such as oils of animal, vegetable, mineral or synthetic origin; fatty substances which are solid at 25° C., such as waxes of animal, vegetable, mineral or synthetic origin; fatty substances in paste form; gums; mixtures thereof.

The compositions according to the invention may thus comprise volatile oils, which evaporate on contact with the skin but whose presence in the cosmetic composition is useful since they make it easier to spread the composition when it is applied to the skin. Spreading agents of this type, referred to here as "volatile oils" are generally oils which, at 25° C., have a saturated vapour pressure at least equal to 0.5 millibar (i.e. 50 Pa). Use is preferably made of oils whose flashpoint is high enough to allow these oils to be used in formulation, and low enough to obtain the desired evanescent effect. Oils whose flashpoint is of the order of 40–100° C. are preferably employed.

Mention may thus be made of volatile silicone oils, such as:

cyclic volatile silicones having 3 to 8, and more preferably 4 to 6, silicon atoms. Examples of these include cyclotetradimethylsiloxane, cyclopentadimethylsiloxane or cyclohexadimethylsiloxane, cyclocopolymers of the dimethylsiloxane/methylalkylsiloxane type, such as Silicone FZ 3109 marketed by the company Union Carbide, which is a dimethylsiloxane/methyloctylsiloxane cyclocopolymer, linear volatile silicones having 2 to 9 silicon atoms. Examples of these include hexamethyldisiloxane, hexylheptamethyltrisiloxane or octylheptamethyltrisiloxane.

Mention may also be made of volatile hydrocarbonoils such as isoparaffins and, in particular, isododecane; and fluorinated oils such as the one marketed under the name GALDEN® (Montefluos).

Use may also be made of non-volatile oils, among which mention may be made of:

poly($C_1$–$C_{20}$)alkylsiloxanes and, in particular, those having trimethylsilyl end groups, preferably those whose viscosity is less than 0.06 $m^2$/s, among which mention may be made of linear polydimethylsiloxanes and alkylmethylpolysiloxanes such as cetyldimethicone (CTFA name), silicones modified with aliphatic and/or aromatic groups, which may or may not contain fluorine, or with functional groups such as hydroxyl, thiol, and/or amine groups, phenylated silicone oils, in particular those of formula:

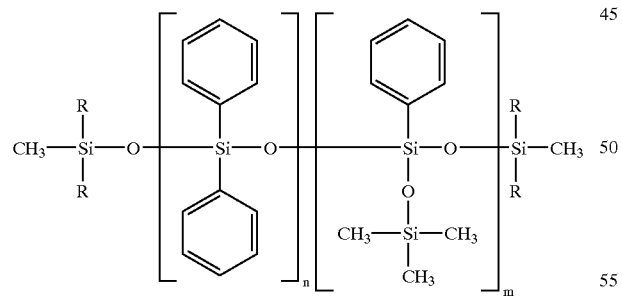

in which R is a $C_1$–$C_{30}$ alkyl radical, an aryl radical or an aralkyl radical, n is an integer ranging from 0 to 100, and m is an integer ranging from 0 to 100, with the condition that the sum of m+n ranges from 1 to 100, oils of animal, vegetable or mineral origin, and in particular animal or vegetable oils formed by fatty acid esters of polyols, in particular liquid triglycerides, for example sunflower oil, corn oil, soybean oil, marrow oil, grapeseed oil, sesame oil, hazelnut oil, apricot oil, almond oil or avocado oil; fish oils, glyceryl tricaprocaprylate, or vegetable or animal oils of formula $R_1COOR_2$ in which $R_1$ represents a higher fatty acid residue containing from 7 to 19 carbon atoms and $R_2$ represents a branched hydrocarbon chain containing 3 to 20 carbon atoms, for example Purcellin oil; liquid paraffin, liquid petroleum jelly, perhydrosqualene, wheatgerm oil, beauty-leaf oil, sesame oil, macadamia oil, grapeseed oil, colza oil, copra oil, groundnut oil, palm oil, castor oil, jojoba oil, olive oil or cereal germ oil; fatty acid esters, alcohols; acetylglycerides; octanoates, decanoates or ricinoleates of alcohols or of polyalcohols; fatty acid triglycerides, glycerides;

fluorinated and perfluorinated oils.

The composition according to the invention may furthermore comprise other fatty substances, which may be selected by the person skilled in the art on the basis of his general knowledge, so as to give the final composition the desired properties, for example in terms of consistency and/or texture. These additional fatty substances may be waxes, gums and/or fatty substances in paste form or of animal, vegetable, mineral or synthetic origin, as well as mixtures thereof.

Mention may, in particular, be made of:

silicone gums, waxes of animal, vegetable, mineral or synthetic origin, such as microcrystalline waxes, paraffin, petrolatum, petroleum jelly, ozokerite, montan wax; beeswax, lanolin and derivatives thereof; candelilla wax, ouricury wax, carnauba wax, japan wax, cocoa butter, cork fibre wax or sugarcane wax; hydrogenated oils which are solid at 25° C., ozokerites, fatty esters and glycerides which are solid at 25° C.; polyethylene waxes and waxes obtained by Fischer-Tropsch synthesis; hydrogenated oils which are solid at 25° C.; lanolins, fatty esters which are solid at 25° C.; silicone waxes; fluorinated waxes.

The composition according to the invention may also comprise one or more organic solvents which are cosmetically acceptable (acceptable in terms of tolerance, toxicology and feel). These organic solvents may represent from 0% to 98% of the total weight of the composition and may be selected from hydrophilic organic solvents, lipophilic organic solvents, amphiphilic solvents or mixtures thereof.

Among the hydrophilic organic solvents, mention may, for example, be made of linear or branched lower monoalcohols having 1 to 8 carbon atoms, such as ethanol, propanol, butanol, isopropanol, isobutanol; polyethylene glycols having 6 to 80 ethylene oxides; polyols such as propylene glycol, isoprene glycol, butylene glycol, glycerol and sorbitol; mono- or dialkyl isosorbide in which the alkyl groups have 1 to 5 carbon atoms; glycol ethers such as diethylene glycol monomethyl or monoethyl ether and propylene glycol ethers such as dipropylene glycol methyl ether. As amphiphilic organic solvents, mention may be made of polyols such as polypropylene glycol (PPG) derivatives such as fatty acid esters of polypropylene glycol and fatty alcohol esters of PPG, for example PPG 23 oleyl ether and PPG-36 oleate. As lipophilic organic solvents, mention may, for example, be made of fatty esters. such as diisopropyl adipate, dioctyl adipate, alkylbenzoates, isopropyl myristate, isopropyl palmitate, butyl stearate, hexyl laurate, isononyl isononanoate, 2-ethylhexyl palmitate, 2-hexyldecyl laurate, 2-octyldecyl palmitate, 2-octyidodecyl myristate, bis(2-hexylethyl)succinate, diisostearyl malate, 2-octyldodecyl lactate, glyceryl triisostearate and diglyceryl triisostearate.

The composition may furthermore comprise a particulate phase, which may comprise pigments and/or pearlescent agents and/or fillers customarily used in cosmetic compositions.

The term pigments should be understood to mean white or coloured, inorganic or organic particles intended to colour and/or opacify the composition. The term fillers should be understood to mean colourless or white, inorganic or synthetic, lamellar or non-lamellar particles intended to give the composition body or rigidity, and/or softness, a matt effect and uniformity when applied as make-up. The term pearlescent agents should be understood to mean iridescent particles which reflect light.

The pigments may be present in the composition at a level, of preferably 0 to 15% by weight of the final composition, and more preferably at a level of 8 to 10% by weight. They may be white or coloured, inorganic and/or organic, and of customary or nanometric size. Mention may be made of the dioxides of titanium, zirconium or cerium, as well as the oxides of zinc, iron or chromium, ferric blue, chromium hydrate, carbon black, ultramarines (aluminosilicate polysulphides), manganese pyrophosphate and certain metal powders such as those of silver or of aluminium, and carbon black. Mention may also be made of the lakes commonly used to give a make-up effect to the lips and the skin, these lakes being salts of calcium, barium, aluminium or zirconium.

The pearlescent agents may be present in the composition at a level of 0 to 20% by weight, preferably in a proportion of the order of 8 to 15% by weight. Examples of the pearlescent agents which may be envisaged include natural mother-of-pearl, mica coated with titanium oxide, with iron oxide, with natural pigment or with bismuth oxychloride, as well as coloured titanium mica.

The fillers, which may be present at a level of from 0 to 30% by weight, more preferably 5 to 15%, in the composition, may be inorganic or synthetic, lamellar or non lamellar. Mention may be made of talc, mica, silica, kaolin, nylon powders and polyethylene powders, Teflon, starch, boron nitride, polymer microspheres such as EXPANCEL (Nobel Industrie), polytrap (Dow Corning) and of silicone resin microbeads (TOSPEARLS from Toshiba for example), precipitated calcium carbonate, magnesium carbonate or hydrocarbonate, metal soaps derived from organic carboxylic acids having 8 to 22 carbon atoms.

The composition may furthermore comprise a colorant, in particular a natural organic colorant such as cochineal carmine, and/or a synthetic colorant such as halo acid, azo or anthraquinone dyes. Mention may also be made of inorganic colorants such as copper sulphate.

The composition may furthermore comprise any additive customarily used in the field of cosmetics, for example antioxidants, fragrances, essential oils, preserving agents, ilipophilic or hydrophilic cosmetic active agents, moisturizers, vitamins, essential fatty acids, sphingolipids, self-tanning agents such as DHA, sunscreens, anti-foaming agents, sequestering agents and antioxidants.

Naturally, the person skilled in the art will take care to select the optional additional compounds, and/or their amount, so that the advantageous properties of the composition according to the invention are not, or not substantially, adversely affected by the addition which is envisaged.

The cosmetic compositions according to the invention are essentially those relating to make-up for the face, that is to say eye-shadows or blushers, eye-liners, mascaras, powders, foundations, tinted creams, lip compositions, and also make-up for the hair, in particular gels, creams or foams for temporary coloration of the hair, and make-up for the nails, in particular aqueous nail varnishes.

The invention is illustrated in more detail in the following examples.

Method of determining the parameter $\Delta E$ using trichromatic coordinates

The photochromic properties of a compound can be characterized in the following way, using the trichromatic coordinates (L, a and b).

The powdered compound is packed in a metal dish.

The trichromatic coordinates (L0, a0, b0) of the packed powder are measured using a Minolta CR300 colorimeter.

The dish is exposed for 30 minutes to a lamp emitting throughout the entire solar spectrum (Heraeus brand Suntest CPS Xenon lamp, reproducing the solar spectrum), then the new coordinates (L30, a30 and b30) are measured which reflect the colour change due It to the exposure.

The parameter $\Delta E30$ is determined in the following way:

$$\Delta E30=[(L30-L0)^2+(a30-a0)^2+(b30-b0)^2]^{1/2}$$

The compound is then placed for 30 minutes in complete darkness, and the colour change is again measured. The parameter $\Delta E60$ is determined in the following way:

$$\Delta E60=[(L60-L0)^2+(a60-a0)^2+(b60-b0)^2]^{1/2}$$

The value $\Delta(\Delta E)$, equal to the absolute value of the difference between $\Delta E60$ and $\Delta E30$, reflects the capacity of a compound to return, after exposure and darkness, to a colour similar to that of the initial state, that is to say before exposure.

EXAMPLE 1

The photochromic compound taken as an example is iron-doped titanium oxide marketed by C.C.I.C. through Ikeda under the name "Photogenica 1".

Its initial characteristics are as follows: $\Delta E30=10.3$ and $\Delta(\Delta E)=2.4$ A mixture is prepared comprising 10% by weight of sodium chloride and 90% by weight of iron-doped titanium oxide. The characteristics of the mixture are measured according to the method below.

The results given in the following table are obtained.

|  | $\Delta E30$ | $\Delta(\Delta E)$ |
| --- | --- | --- |
| Iron-doped titanium oxide | 10.3 | 2.4 |
| 90% iron-doped titanium oxide + 10% NaCl | 12.0 | 4.6 |

It is therefore seen that the addition of 10% sodium chloride makes it possible to obtain a gain of more than 15% in terms of the colour change of the titanium oxide; more than 90% reversibility in the photochromism phenomenon is also obtained.

EXAMPLE 2

The characteristics of the mixtures below are measured according to Example 1.

|  | $\Delta E30$ |
| --- | --- |
| Iron-doped titanium oxide + 10% glycerine | 17.1 |
| Iron-doped titanium oxide + 10% glycerine + 10% LiCl | 20.9 |

The addition of lithium chloride makes it possible to obtain a gain of more than 20% in terms of the colour change.

EXAMPLE 3

A powder having the following composition is prepared:

| | |
|---|---|
| talc | 30 g |
| mica | 20 g |
| nylon powder | 16 g |
| zinc stearate | 4 g |
| iron oxide | 2 g |
| photochromic iron-doped titanium oxide | 10 g |
| bismuth oxychloride | 10 g |
| fatty binder | 8 g |

A composition having photochromic properties characterized by a $\Delta E30$ of 2.5 is obtained.

When 15 g of sodium chloride are added to this composition, a composition is obtained having good cosmetic properties and exhibiting a $\Delta E30$ more than 50% higher than that of the previous composition.

I claim:

1. A method comprising the step of mixing an ionic conductor with a cosmetic composition comprising at least one inorganic photochromic compound and a cosmetically acceptable medium to improve the photochromism of said cosmetic composition, the amount of said ionic conductor being effective to improve said photochromism.

2. A method according to claim 1, wherein said ionic conductor increases the $\Delta E30$ of said cosmetic composition.

3. A method according to claim 1, wherein said ionic conductor increases the $\Delta(\Delta E)$ of said cosmetic composition.

4. A cosmetic composition comprising at least one ionic conductor and at least one inorganic photochromic compound and a cosmetically acceptable medium, said ionic conductor being present in an amount effective to improve the photochromism of said photochromic compound.

5. A cosmetic composition according to claim 4, wherein said at least one ionic conductor is selected from alkali metal salts and alkaline-earth metal salts.

6. A cosmetic composition according to claim 5, wherein said at least one ionic conductor is selected from the chlorides of sodium, lithium, potassium, and the sulphates of magnesium and calcium.

7. A cosmetic composition according to claim 4, wherein said at least one ionic conductor is present in said cosmetic composition in an amount ranging from 0.5 to 30% by weight relative to the total weight of said cosmetic composition.

8. A cosmetic composition according to claim 7, wherein said at least one ionic conductor is present in said cosmetic composition in an amount ranging from 1 to 20% by weight relative to the total weight of said cosmetic composition.

9. A cosmetic composition according to claim 4, wherein said at least one photochromic inorganic compound is selected from metal oxides, metal oxide hydrates and doped aluminosilicates.

10. A cosmetic composition according to claim 9, wherein said metal oxides are selected from the oxides of titanium, niobium, silicon, aluminium, zinc, hafnium, thorium, tin, thallium, zirconium, beryllium, cobalt, calcium and magnesium.

11. A cosmetic composition according to claim 9, wherein said at least one photochromic inorganic compound is selected from oxides and hydrated oxides of titanium, aluminium, zinc, zirconium, calcium and magnesium.

12. A cosmetic composition according to claim 11, wherein said at least one photochromic inorganic compound is selected from titanium dioxide.

13. A cosmetic composition according to claim 4, wherein said at least one photochromic inorganic compound is present in said cosmetic composition in an amount ranging from 0.01 to 30% by weight relative to the total weight of said cosmetic composition.

14. A cosmetic composition according to claim 13, wherein said at least one photochromic inorganic compound is present in said cosmetic composition in an amount ranging from 1 to 15% by weight relative to the total weight of said cosmetic composition.

15. A cosmetic composition according to claim 4, wherein said cosmetic composition is to be applied to mucous membranes, mucocutaneous tissues and keratinous tissues.

16. A cosmetic composition according to claim 4, wherein said cosmetic composition is to be applied to skin and parts of the exoskeleton.

17. A cosmetic composition according to claim 4, wherein said cosmetic composition is a make-up or care product for skin, a suncare or self-tanning product, or a haircare product.

18. A cosmetic composition according to claim 4, wherein said cosmetic composition is a lip composition, fourndation, blusher, eyeshadow, eyeliner, mascara, or nail varnish.

19. A cosmetic composition according to claim 4, wherein said cosmetically acceptable medium is in the form of a suspension, a dispersion, or a solution in an aqueous or aqueous-alcohol medium; an oil-in-water, water-in-oil, or multiple emulsion; a gel or foam; an emulsified gel; a dispersion of vesicles; a two-phase or multi-phase lotion; or a spray.

20. A cosmetic composition according to claim 19, wherein said vesicles are lipid vesicles.

21. A cosmetic composition according to claim 19, wherein said suspension, dispersion, or solution in an aqueous or aqueous-alcohol medium is gelled or thickened.

22. A cosmetic composition according to claim 4, wherein said composition comprises an aqueous phase.

23. A cosmetic composition according to claim 4, wherein said composition is in the form of a dispersion, an emulsion, a gel or an aqueous or aqueous-alcoholic solution.

24. A cosmetic composition according to claim 22, wherein said aqueous phase comprises from 0 to 14% by weight, relative to the total weight of said aqueous phase, of at least one compound selected from a $C_2$–$C_6$ lower monoalcohol and a polyol.

25. A cosmetic composition according to claim 24, wherein said polyol is selected from glycerol, butylene glycol, isoprene glycol, propylene glycol, and polyethylene glycol.

26. A cosmetic composition according to claim 4, wherein said cosmetic composition is in the form of an emulsion and comprises at least one surfactant as an emulsifier.

27. A cosmetic composition according to claim 26, wherein said at least one surfactant is present in an amount ranging from 0.01 to 30% by weight relative to the total weight of said composition.

28. A cosmetic-composition according to claim 26, wherein said composition in the form of an emulsion further comprises at least one co-emulsifier.

29. A cosmetic composition according to claim 28, wherein said at least one co-emulsifier is present in an amount up to 5% by weight relative to the total weight of said composition.

30. A cosmetic composition according to claim 28, wherein said at least one co-emulsifier is selected from oxyethylenated sorbitan monostearate, fatty alcohols and fatty acid esters of polyols.

31. A cosmetic composition according to claim 30, wherein said fatty alcohols are selected from stearyl alcohol and cetyl alcohol.

32. A cosmetic composition according to claim 30, wherein said fatty acid ester is glyceryl stearate.

33. A cosmetic composition according to claim 4, wherein said cosmetic composition further comprises at least one thickener.

34. A cosmetic composition according to claim 33, wherein said at least one thickener is present in an amount up to 6% by weight, relative to the total weight of said cosmetic composition.

35. A cosmetic composition according to claim 4, wherein said cosmetic composition further comprises at least one film-forming polymer.

36. A cosmetic composition according to claim 35, wherein said film-forming polymer is dissolved or dispersed in a cosmetically acceptable medium.

37. A cosmetic composition according to claim 35, wherein said at least one film-forming polymer is selected from mitrocellulose, cellulose acetobutyrate, polyvinyl butyrals, it alkyl resins, polyesters, acrylics, vinyls, and polyurethanes.

38. A cosmetic composition according to claim 4, wherein said composition further comprises at least one plasticizer.

39. A cosmetic composition according to claim 38, wherein said at least one plasticizer is present in an amount ranging from 1 to 40% by weight, relative to the total weight of said cosmetic composition.

40. A cosmetic composition according to claim 4, wherein said cosmetic composition comprises a fatty phase.

41. A cosmetic composition according to claim 4, wherein said cosmetic composition comprises at least one cosmetically acceptable organic solvent.

42. A cosmetic composition according to claim 4, wherein said cosmetic composition further comprises a particulate phase.

43. A cosmetic composition according to claim 42, wherein said particulate phase comprises a pigment, a pearlescent agent or a filler.

44. A cosmetic composition according to claim 43, wherein said pigment is present in an amount up to 15% by weight, relative to the total weight of said cosmetic composition.

45. A cosmetic composition according to claim 44, wherein said pigment is present in an amount ranging from 8 to 10% by weight, relative to the total weight of said cosmetic composition.

46. A cosmetic composition according to claim 43, wherein said pearlescent agent is present in an amount up to 20% by weight, relative to the total weight of said cosmetic composition.

47. A cosmetic composition according to claim 46, wherein said pearlescent agent is present in an amount ranging from 8 to 15% by weight, relative to the total weight of said cosmetic composition.

48. A cosmetic composition according to claim 43, wherein said filler is present in an amount up to 30% by weight, relative to the total weight of said cosmetic composition.

49. A cosmetic composition according to claim 48, wherein said filler is present in an amount ranging from 5 to 15% by weight, relative to the total weight of said cosmetic composition.

50. A cosmetic composition according to claim 4, wherein said cosmetic composition further comprises at least one colorant.

51. A cosmetic composition according to claim 50, wherein said at least one colorant is selected from cochineal carmine, halo acid, azo and anthraquinone dyes and copper sulphate.

52. A cosmetic composition according to claim 4, wherein said cosmetic composition further comprises at least one cosmetically acceptable additive.

53. A cosmetic composition according to claim 4, wherein said cosmetic composition is a lipstick; a tinted cream; a powder, a gel, cream or foam for temporary coloration of hair; or an aqueous nail varnish.

* * * * *

UNITED STATES PATENT AND TRADEMARK OFFICE
CERTIFICATE OF CORRECTION

PATENT NO. : 6,468,550 B1
DATED : October 22, 2002
INVENTOR(S) : Christophe Remy It is certified that error appears in the above-identified patent and that said Letters Patent is hereby corrected as shown below:

<u>Title page,</u>
Item [57], ABSTRACT,
Line 1, "photochromishm" should read -- photochromism --.

<u>Column 12,</u>
Line 54, "cosmetic-composition" should read -- cosmetic composition --.

<u>Column 13,</u>
Line 17, "mitrocellulose" should read -- nitrocellulose --.

Signed and Sealed this

Twenty-second Day of July, 2003

JAMES E. ROGAN
*Director of the United States Patent and Trademark Office*